United States Patent [19]

Babaev

[11] Patent Number: 5,076,266

[45] Date of Patent: Dec. 31, 1991

[54] DEVICE FOR ULTRASONIC ATOMIZING OF LIQUID MEDIUM

[75] Inventor: Eilaz P. O. Babaev, Baku, U.S.S.R.

[73] Assignee: Azerbaidzhansky Politekhnichesky Institut Imeni CH. Ildryma, Baku, U.S.S.R.

[21] Appl. No.: 460,344

[22] PCT Filed: Apr. 19, 1989

[86] PCT No.: PCT/SU89/00096

§ 371 Date: May 16, 1990

§ 102(e) Date: May 16, 1990

[87] PCT Pub. No.: WO90/12655

PCT Pub. Date: Nov. 1, 1990

[51] Int. Cl.[5] .................... A61M 11/00; B05B 17/06

[52] U.S. Cl. .................... 128/200.16; 128/200.14

[58] Field of Search .................... 128/200.14, 200.16

[56] References Cited

U.S. PATENT DOCUMENTS 1,979,006 10/1934 Moran .................... 128/200.18

4,726,525 2/1988 Yonekawa et al. .................... 239/102.2

FOREIGN PATENT DOCUMENTS 2480143 10/1981 France .

1237261 6/1986 U.S.S.R. .

1438850 11/1988 U.S.S.R. .

*Primary Examiner*—Edgar S. Burr

*Assistant Examiner*—Lisa E. Malvaso

*Attorney, Agent, or Firm*—Fleit, Jacobson, Cohn, Price, Holman & Stern

[57] ABSTRACT

A device for ultrasonic atomization of a liquid medium comprises an ultrasonic vibrator (1) with a concentrator (2) whose terminal portion (4) accommodates a bell mouth (24) which serves as a means for regulating the liquid medium spray cone angle. Main, additional, and auxiliary thrust bushings (3,5,6) are installed on the ultrasonic vibrator (1) and concentrator (2). Arranged along the concentrator (2) are a branch pipe (9) for feeding a liquid medium and a guide (8) mechanically connected with the main and additional thrust bushings (3 and 5) whose free ends extend through respective hollow rods (15 and 16) mechanically linked with the auxiliary thrust bushing (6).

8 Claims, 2 Drawing Sheets

DEVICE FOR ULTRASONIC ATOMIZING OF LIQUID MEDIUM

FIELD OF THE INVENTION

The present invention relates to devices for atomizing a liquid medium and in particular to devices for ultrasonic atomizing of a liquid medium.

BACKGROUND ART

Modern ultrasonics lack appropriate devices for ultrasonic atomizing of a liquid medium, which would provide a fairly long spray cone without heating. Moreover, difficulties are generally involved in obtaining a uniform spray.

There is known a device for ultrasonic atomizing of a liquid medium (SU, A, 1,237,261) comprising an ultrasonic vibrator with a concentrator, a main thrust bushing installed on the ultrasonic vibrator, an additional thrust bushing installed on the concentrator, an auxiliary thrust bushing having a radial channel with an outlet on its internal surface and disposed in the terminal portion of the concentrator, a guide mechanically connected to the main and additional thrust bushings, a branch pipe for feeding a liquid medium, which is arranged along the longitudinal axis of the concentrator and mechanically connected to the main thrust bushing, a free end of said branch pipe being fitted through the additional thrust bushing, and two hollow rods, one of which is mechanically connected to the auxiliary thrust bushing, while the other one communicates with its radial channel, free ends of the guide and the branch pipe for feeding a liquid medium being movably fitted in the other ends of the first and second hollow rods, respectively.

However, in the known device a desired liquid-medium spray-cone angle may be obtained only by using an ultrasonic vibrator having a predetermined power, a disadvantage increasing ineffectively a spray-cone angle due to which the spray length is limited and dispersion is appreciably decreased.

Moreover, the foregoing device has been generally unsatisfactory due to the fact that a liquid medium is atomized at a spray-cone angle formed in the course of its free movement from the concentrator, a factor making the spray nonuniform and unstable.

DISCLOSURE OF THE INVENTION

This invention is based on the problem of providing a device for ultrasonic atomizing of a liquid medium, equipped with a means to increase the spray length, make the spray of the liquid medium more uniform and stable.

This problem is accomplished by that a device for ultrasonic atomizing of a liquid medium, comprising an ultrasonic vibrator with a concentrator, a main thrust bushing installed on the ultrasonic vibrator, an additional thrust bushing installed on the concentrator, an auxiliary thrust bushing having a radial channel with an outlet on its internal surface and disposed in the terminal portion of the concentrator, a guide mechanically connected to the main and additional thrust bushings, a branch pipe for feeding a liquid medium, which is arranged along the longitudinal axis of the concentrator and connected mechanically to the main thrust bushing, a free end of said branch pipe being fitted through the additional thrust bushing, and two hollow rods, one of which is mechanically connected to the auxiliary thrust bushing, while the other one communicates with its radial channel, free ends of the guide and the branch pipe for feeding a liquid medium being movably fitted in the other ends of the first and second hollow rods, respectively, which, according to the invention, comprises a means for regulating a liquid-medium spray-cone angle, which is arranged in the terminal portion of the concentrator.

It is preferable that in the proposed device for ultrasonic atomizing of a liquid medium said means for regulating a liquid-medium spray-cone angle should be made as a bell mouth encompassing coaxially with a gap the terminal portion of the concentrator and attached to the auxiliary thrust bushing with its smaller end.

It is also preferable that in the proposed device for ultrasonic atomizing of a liquid medium said bell mouth should be secured to the end of the auxiliary thrust bushing facing the additional thrust bushing.

It is advantageous that in the proposed device for ultrasonic atomizing of a liquid medium said bell mouth should be secured to the end of the auxiliary thrust bushing nearest to terminal portion of the concentrator.

It is also advantageous that in the proposed device for ultrasonic atomizing of a liquid medium the end of the terminal portion of the concentrator should act as said means for regulating a liquid-medium spray-cone angle.

It is further advantageous that in the proposed device for ultrasonic atomizing of a liquid medium the end of the terminal portion of the concentrator should be cone-shaped.

It is advisable that in the proposed device for ultrasonic atomizing of a liquid medium the end of the terminal portion of the concentrator should be a truncated cone.

It is also advisable that in the proposed device for ultrasonic atomizing of a liquid medium the end of the terminal portion of the concentrator should constitute a part of the surface of an ellipsoid of revolution.

The present invention permits decreasing a liquid-medium spray-cone angle whereby the spray length is substantially increased, an advantage intensifying dispersion of said liquid medium.

Moreover, the invention makes it possible to produce a bunch-spray in atomizing a liquid medium due to which ejection occurs, a factor making said spray more uniform and stable.

BRIEF DESCRIPTION OF DRAWINGS

Other objects and advantages of the invention will become more readily apparent from the description of preferred embodiments thereof, taken in conjunction with the accompanying drawings wherein.

BEST MODE FOR CARRYING THE INVENTION

Figure 1:
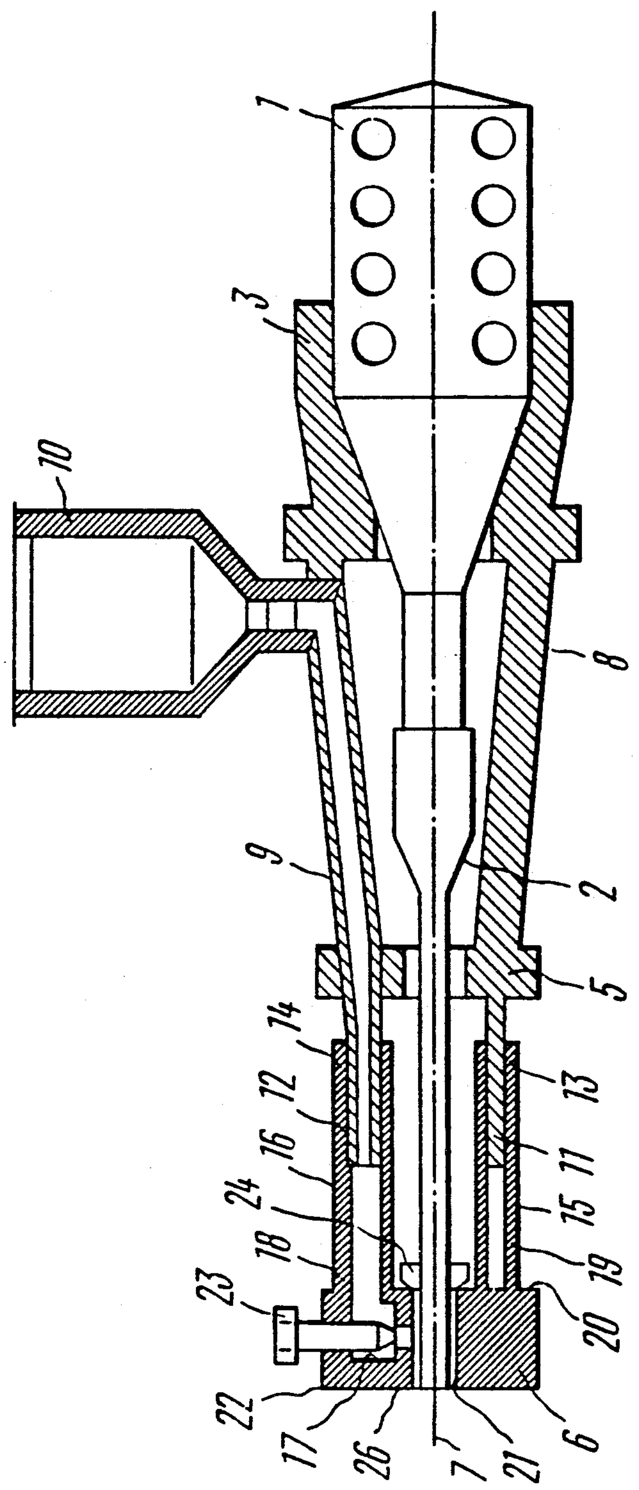
FIG. 1 is a general view (longitudinal section) of a device for ultrasonic atomizing of a liquid medium according to the invention.
Figure 2:
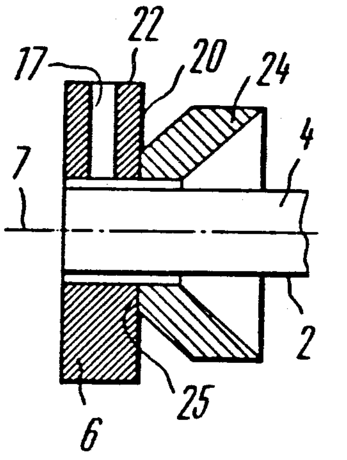
FIG. 2 is an enlarged longitudinal section of a terminal portion of a concentrator with an auxiliary thrust bushing and a bell mouth according to the invention.

The device for ultrasonic atomizing of a liquid medium forming the subject of the present invention comprises an ultrasonic vibrator 1 (FIG. 1) with a concentrator 2. The ultrasonic vibrator 1 mounts a main thrust bushing 3, while the concentrator 2 and its terminal portion 4 accommodate, respectively, an additional thrust bushing 5 and an auxiliary thrust bushing 6. Arranged along a longitudinal axis 7 of the concentrator 2 are a guide 8 and a branch pipe 9 for feeding a liquid medium. A tank 10 holding a liquid medium is in communication with said branch pipe. The guide 8 and the branch pipe 9 rest against the bushing 3. Free ends 11 and 12 of the guide 8 and the branch pipe 9 respectively, are fitted through the bushing 5 and movably inserted, respectively, in ends 13 and 14 of corresponding hollow rods 15 and 16. The bushing 6 has a radial channel 17 whose inlet communicates with another end 18 of the rod 16, while an end 19 of the rod 15 is secured to an end 20 of the bushing 6. The outlet of the channel 17 is found on an internal surface 21 (FIG. 2) of the bushing 6. An external surface 22 (FIG. 1) of the bushing 6 has an opening accommodating a valve 23 for regulating the feed of a liquid medium, said valve being in communication with the end 18 of the rod 16. The means for regulating a liquid-medium spray-cone angle represents a bell mouth 24 (FIGS. 1 and 2) secured coaxially with a gap with its smaller end 25 to the end 20 of the bushing 6 facing the bushing 5.

Figure 3:
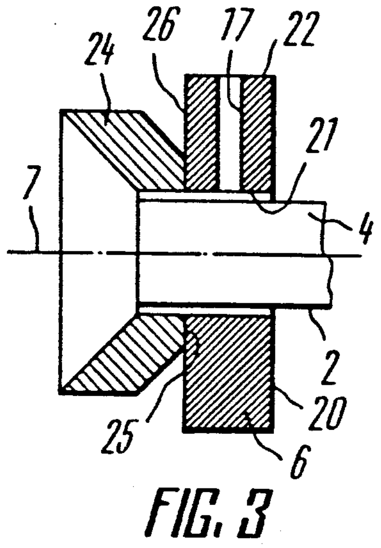
FIG. 3 shows the terminal portion of the concentrator with the auxiliary thrust bushing of FIG. 2 and with the bell mouth secured to the end of the auxiliary thrust bushing nearest to the end of the terminal portion of the concentrator (an enlarged longitudinal section) according to the invention.

In another embodiment of the device for ultrasonic atomizing of a liquid medium, the end 25 (FIG. 3) of the bell mouth 24 is secured to an end 26 (FIGS. 1 and 3) of the bushing 6. Other design features thereof are similar to those described above.

Figure 4:
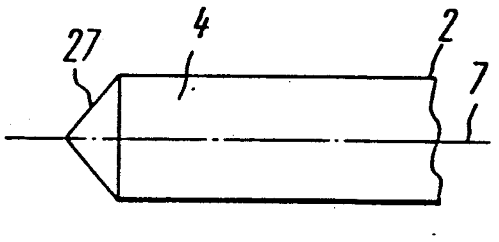
FIG. 4 shows on an enlarged scale the end of the terminal portion of the concentrator shaped as a cone according to the invention.
Figure 5:
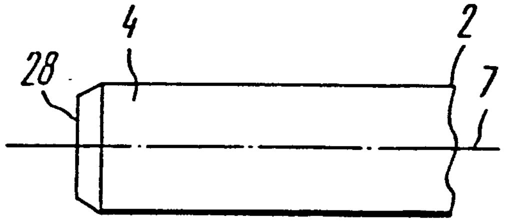
FIG. 5 shows on an enlarged scale the end of the terminal portion of the concentrator shaped as a truncated cone according to the invention.
Figure 6:
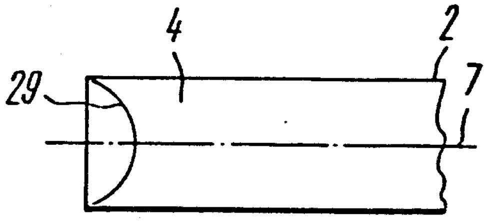
FIG. 6 shows on an enlarged scale the end of the terminal portion of the concentrator constituting a part of the surface of an ellipsoid of revolution according to the invention.

FIGS. 4, 5 and 6 illustrate preferred embodiments of the means for regulating a liquid-medium spray-cone angle, which is formed with the end of the terminal portion 4 of the concentrator 2.

Referring to FIG. 4 an end 27 of the portion 4 of the concentrator 2 is cone-shaped.

Turning to FIG. 5 an end 28 of the portion 4 of the concentrator 2 is shaped as a truncated cone.

In the embodiment illustrated in FIG. 6 an end 29 of the portion 4 of the concentrator 2 constitutes a part of the surface of an ellipsoid of revolution.

The proposed device for ultrasonic atomizing of a liquid medium operates in the following manner.

An ultrasonic generator (not shown in the drawing) feeds signals to the ultrasonic vibrator 1 (FIG. 1), thereby inducing ultrasonic vibrations therein. From the vibrator 1 said vibrations are transmitted to the concentrator 2 to be radiated from its terminal portion 4. At the same time, a liquid medium is supplied from the tank 10 through the branch pipe 9 to the portion 4 of the concentrator 2. From the branch pipe 9 said liquid medium is supplied through the hollow rod 16 to the radial channel 17 of the auxiliary thrust bushing 6. Thereafter said liquid medium is fed from the outlet of the channel 17 to the portion 4 of the concentrator 2. The bell mouth 24 acting as the means for regulating a spray-cone angle produces ejection due to which the spray of said liquid medium will be more stable and uniform.

When the bell mouth 24 is found on the end 20 (FIGS. 1 and 2) of the bushing 6, the spray-cone angle decreases, a factor increasing the spray-cone length and improving the mixing of heterogeneous liquids.

When the bell mouth 24 is found on the end 25 (FIG. 3) of the bushing 6, the spray-cone angle may be adjusted to a great value required with a stable and uniform spray in atomizing said liquid medium bring essentially unchanged.

Consider now operation with the end of the concentrator 2 serving as said means for regulating the spray-cone angle.

With the cone-shaped end 27 (FIG. 4) or the end 29 (FIG. 6) constituting a part of the surface of an ellipsoid of revolution, a drop or spray of said liquid medium is delivered to the ends 27 and 29, whence it is atomized at one point, which permits bunch spraying of said liquid medium.

When use is made of the end 28 (FIG. 5) shaped as a truncated cone, the spray bunch diameter may be adjusted as required.

The bell mouth 24 arranged on the end 20 of the bushing 6 may be used with other embodiments of the end of the concentrator 2 (not shown in the drawing) mentioned above. The afore-mentioned advantages will thus be combined.

The present invention allows regulation of a liquid-medium spray-cone angle whereby the length of a spray of said liquid medium may be adjusted as required.

INDUSTRIAL APPLICABILITY

This invention may be used as an aerosol and fog producing means in applying liquid media to various surfaces.

It is also suitable for use in internal combustion engines, injectors etc.

I claim:

1. A device for ultrasonic atomizing of a liquid medium, comprising:

an ultrasonic vibrator (1) communicating with a concentrator (2);

a main thrust bushing (3) wherein the ultrasonic vibrator (1) is mounted;

an additional thrust bushing (5) encompassing the concentrator (2);

an auxiliary thrust bushing (6) whose body has a radial channel (17) whose outlet is on an internal surface (21) of the bushing which encompasses a terminal portion (4) of the concentrator (2);

a guide (8) mechanically connected with the main and additional thrust bushing (3 and 5) and having a free guide end;

a branch pipe (9) to feed a liquid medium, which is arranged along a geometrical longitudinal axis (7) of the concentrator (2), and is mechanically connected to the main thrust bushing, (3) and has a free end (12) extending through the additional thrust bushing (5);

two hollow rods (15,16) each having one end mechanically connected with the auxiliary thrust bushing (6) and having distal ends (13, 14) into which are movably inserted the free end of the guide (8) and the branch pipe (9) wherein the rod, into which the branch pipe is inserted, is associated with the radial channel (17) for feeding a liquid medium to the terminal end of the concentrator; and a means for regulating a liquid medium spray cone angle, which arranged concentric with and on said terminal portion (4) of the concentrator (2) to provide a uniform spray with a selected cone angle.

2. A device as claimed in claim 1, in which the means for regulating the spray cone angle include a bell mouth (24) coaxially encompassing the terminal portion (4) of the concentrator (2) with a gap and secured, by the smaller end thereof, to the auxiliary thrust bushing (6).

3. A device as claimed in claim 2, in which the bell mouth (24) is secured to an end (20) of auxiliary thrust bushing (6), facing the additional thrust bushing (5).

4. A device as claimed in claim 2, in which the bell mouth (24) is secured to an end of the auxiliary thrust bushing (6), facing away from the additional thrust bushing (5).

5. A device as claimed in claim 1, in which the means for regulating the liquid medium spray cone angle include a convex configuration at the end of the concentrator (2) at the terminal portion (4) for providing such uniform spray with selected cone angle.

6. A device as claimed in claim 5, in which the end (27) of the concentrator (2) of the terminal portion (4) is cone-shaped.

7. A device as claimed in claim 5, in which the end of the concentrator (2) at the terminal portion (4) is shaped as a truncated cone.

8. A device as claimed in claim 5, in which the end (29) of the concentrator (2) at the terminal portion (4) is chisel-shaped.

* * * * *